United States Patent [19]

Wang

[11] Patent Number: 4,857,055
[45] Date of Patent: Aug. 15, 1989

[54] COMPRESSION DEVICE ENABLING FLEXIBLE SOLUTION CONTAINERS TO PRODUCE CONSTANT DELIVERY RATE

[76] Inventor: Paul Y. Wang, 47 Marblemount Crescent, Agincourt, Ontario, Canada, M1T 2H5

[21] Appl. No.: 38,244

[22] Filed: Apr. 14, 1987

[30] Foreign Application Priority Data

Apr. 15, 1986 [CA] Canada ................ 506759

[51] Int. Cl.⁴ .................................. A61M 37/00
[52] U.S. Cl. ........................ 604/133; 604/141; 222/95
[58] Field of Search ............ 222/386.5, 95, 389; 128/DIG. 12; 604/131, 132, 140, 141, 145

[56] References Cited

U.S. PATENT DOCUMENTS

| | | | |
|---|---|---|---|
| 2,876,768 | 3/1959 | Schultz | 604/141 |
| 3,153,414 | 10/1964 | Beall et al. | 222/95 |
| 3,486,539 | 12/1969 | Jacuzzi | 604/132 |
| 3,640,277 | 2/1972 | Adelberg | 604/141 |
| 4,337,769 | 7/1982 | Olson | 604/131 |
| 4,539,005 | 9/1985 | Greenblat | 128/DIG 12 |
| 4,557,728 | 12/1985 | Sealfon et al. | 222/95 |
| 4,673,392 | 6/1987 | Keime | 128/DIG. 12 |

Primary Examiner—Jerome L. Kruter
Attorney, Agent, or Firm—Ostrolenk, Faber, Gerb & Soffen

[57] ABSTRACT

A compression device, which enables standard-size flexible solution containers to infuse at a constant flow rate, comprises a rigid external casing, in combination with two leak-proof sacs inflatable by a low pressure gas, and a flow moderator system. The flexible solution container must be positioned evenly in-between the inflatable sacs in order to obtain constant delivery rate while discharging about 80% of its intended maximum content. Flow moderators connected in series with by-passes can provide flow rates in discrete steps. The disposable compression device is adaptable to drug infusion and fluid replenishment therapy.

12 Claims, 1 Drawing Sheet

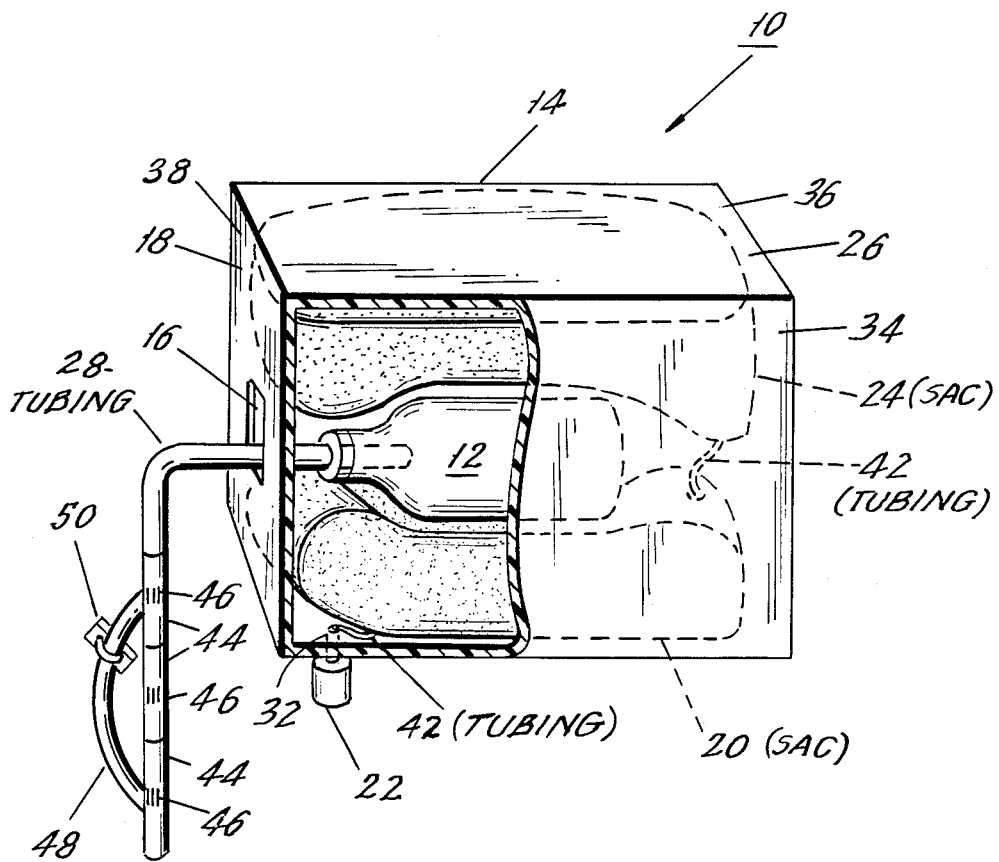

COMPRESSION DEVICE ENABLING FLEXIBLE SOLUTION CONTAINERS TO PRODUCE CONSTANT DELIVERY RATE

FIELD OF THE INVENTION

This invention relates to a disposable compression device which enables conventional drug solution bags to achieve a constant flow rate during infusion, over the period of time necessary to discharge about 80% of its initial content.

BACKGROUND OF THE INVENTION

In taking a drug, oral ingestion is the simplest form of administration. However, this route of intake is applicable mostly to low molecular weight compounds which are relatively stable at the pH of the stomach and gastrointestinal tract. Life-saving drugs such as insulin for the treatment of diabetes mellitus, and heparin for anticoagulation in cardiovascular diseases, are macromolecules which are susceptible to proteolytic enzymes or cannot be absorbed through the intestinal wall, if taken orally. Therefore, these drugs can only be administered by injection which imparts too high an initial concentration that may decrease rapidly with reduced therapeutic efficiency. The alternative is to infuse a dilute solution of the drug over the period of time during which therapy is desired.

BRIEF REFERENCE TO THE PRIOR ART

For many years, glass bottles or flexible poly-(vinyl chloride) bags have been used as drug solution containers which must be elevated above the patient in order to infuse the solution by gravity. Because the decreasing solution level changes the hydrostatic pressure, the flow rate is not constant and must be adjusted repeatedly by loosening a clamp to remain near a chosen value. If a flow rate higher than conveniently obtainable by gravity alone is required, steps must be taken to speed up the flow rate. The plastic solution bag is then put inside a pocket next to a rubber bladder. After being pumped up manually by squeezing an elastic bulb, the distended bladder presses on the solution container to raise the flow which, however, soon decays unless the bladder is pumped again.

More recently, battery-powered portable pumps are used to infuse insulin into diabetic patients. Although capable of variable delivery rates, these complicated pumps have a reservoir volume of less than 6 ml, which is unsuitable for fluid replenishment, antibiotic or other therapy where a high flow rate is required such as in emergency or ambulatory situations. In addition, the cost of these small pumps is very high which limits the affordability to a few selected individuals.

An alternative is the variable rate peristaltic pumps which are expensive as well as bulky, and must be mounted on a sturdy pole close to the patient's bed. Further, the large pump motor must be plugged into a wall socket to operate, thus severely restricting the mobility of the patient, especially during later stages of convalescence when exercise is encouraged to aid morale and speed recovery.

A satisfactory infusion device must be compact, simple to operate and very light so that it can reasonably be carried by patients who are usually not physically strong enough to cope with an extraneous load. It should also be powered by a dependable energy source, and have several discrete flow rates that remain constant, once selected. As well, the device should alleviate the shortcomings of the current mode of drug solution infusion by the commonly used plastic bags through improving upon its time-dependent decay of flow rate, rather than completely replacing it. Therefore, for whatever reason, if it were decided to revert back to the infusion from the plastic bag through gravity drain, the choice could be readily implemented. Finally, low cost must not be overlooked, so that its availability will not be limited to a selected few.

DESCRIPTION OF A PREFERRED EMBODIMENT

It is an object of the present invention to provide a novel compression device which will enable the conventional flexible containers for drug solution to infuse at a constant flow rate.

It is a further object of the present invention to provide an infusion system which satisfies one or more of the above criteria.

The present invention provides a compression device to which will squeeze out the solution at a constant flow rate from a flexible plastic bag 12 in common use in the hospital, without the need for the intermittent adjustment otherwise required when the plastic bag containing the solution drains by gravity. In one embodiment, the device is an 18 cm×10 cm×5 cm box 14 with a 3.5 cm by 1 cm hole 16 cut in the centre of one of the 5 cm×10 cm sides 18 of the box. There is a leak-proof sac 20 at the bottom of the box which is inflatable to a volume of 900 mL by an aerosol propellant 22. Another similar inflatable leak-proof sac 24 is to be pressed downward later with the top lid 26. When infusion at a constant flow rate is required, the plastic bag 12 containing the drug solution is placed in the 14 box and the exit ports 28 for the solution are led through the 3.5 cm by 1 cm hole on the side of the box as aforementioned. After the upper sac 24 with the top lid of the box 26 is superimposed on the drug solution bag, 12 and the lid 26 is securely closed, a valve on the aerosol propellant canister is opened to inflate the two leak-proof sacs 20, 24. Because the pressure of the gas remains essentially constant even when there is slight fluctuation in ambient temperature, the compression exerted on the flexible solution 12 container positioned in-between the two inflated sacs changes little as well. Consequently, a constant flow rate of the solution discharging from the container is realized. However, if one of the inflatable sacs is omitted, the flow rate of solution from the flexible container will decay progressively even though the pressure inside the remaining inflatable sac is not altered.

The external rigid casing 14 of the compression device is made from 2.5 mm thick plastic sheets, preferably optically clear. The leak-proof inflatable sacs 20, 24 are made by heat sealing of heavy-duty polyethylene films which also have good optical clarity and at the same time are resistant to swelling when in contact with a aerosol propellant. The transparency will allow visualization of the internal contents of the drug solution bag, which is always inspected at regular intervals during use for the presence of particulate suspension or air bubbles that may develop and be harmful. The oversized capacity of the two inflatable sacs is chosen to accommodate the different sizes of the drug solution bag 12 made of poly-(vinyl chloride) currently used in hospitals. The common sizes of these solution infusion bags may vary from 50 mL to 250 mL in capacity. Therefore, regardless of the size of the standard drug infusion bag to be placed in the compression device of the instant invention, a good fit to ensure a constant top-and-bottom compression is readily achieved and, thus, constant flow rate of the solution from the flexible container is assured.

In assembling the plastic box, 2 pieces 34, 36 and 38, respectively each of the 18 cm×10 cm, 18 cm×5 cm, and 10 cm×5 cm panels of the 2.5-mm thick transparent plastic sheet are cut. Many rigid but transparent plastic materials such as acrylic, polystyrene, unplasticized poly-(vinyl chloride) and polycarbonate may be used. In addition, a combination of the said transparent plastic panels and non-optically clear material such as nylon, acrylonitrile-butadiene-styrene co-polymer or the like may also be used in combination with the others aforementioned as long as visualization of the internal content of the drug solution bag is not completely obstructed. The acrylic plastic panels can be glued together by methyl α-cyanoacrylate adhesive and the assembled box can be ready for use in a few minutes. Other appropriate adhesives may be chosen such as epoxy resin, peroxide-catalyzed polyester resin in styrene, oxygen-retarded acrylic formulation or the like which is known, to those skilled in the art, to form good bonds on the rigid materials aforementioned. The heavy-duty polyethylene films ar heat sealed by a standard hot press of the type known as Audion Futura Portable T-2 (Cole-Palmer & Co., Chicago, Il). The leak-proof inflatable sacs are further connected in series by a short length of flexible polyethylene tubing (I.D.: 1 mm) 42. The sac to be placed in the bottom of the box has an additional flexible polyethylene tubing 44 sealed thereto which serves as a connector, through the 3.5 cm×1 cm hole on the end side of the rigid casing of the device, to the valve 32 on the volatile propellant canister 22 affixed to the exterior side of the rigid casing. One of the leak-proof inflatable sacs is then attached to the bottom of the rigid box by double-faced adhesive tape, and the other is positioned over the solution container before the box is closed by the top panel. When many of the compression device of the instant invention are required, the external casing and its two inflatable sacs may be made by injection or other molding techniques.

The constant compression device of the present invention may be used together with flow moderators connected to the drug solution bag in series to provide a selection of discrete flow rates from about 60 mL/hr to 11 mL/hr. Customarily, the standard poly-(vinyl chloride) drug infusion bags are used with tubings having a pinch clamp which must be loosened manually from time to time to balance the decaying flow rate as the solution becomes depleted gradually over time. The adjustment of flow rate by the pinch-clamp is often arbitrary and as a consequence the recipient may be given fluctuating amounts of the medicament-containing fluid. More dependably, the flow rate of an infusion solution can be moderated to one desired level by a length of capillary tubing according to the Poiseulle equation. However, in hospital use, some selection of flow rates which can be individually maintained at a constant level is often required. It is preferable therefore to use sections of small tubes packed with fibres to act as a resistor which can moderate flow in discrete steps when several are connected in a series with bypasses.

Suitable flow moderator units can be made by pulling a bundle of folded fibres 46 into the lumen of a flexible polyethylene tubing 44 (I.D.: 1.5 mm; wall thickness: 0.5 mm). A 40-cm long nylon thread diameter: 0.3 mm) is folded at its mid-point which is then pushed through the 7-cm long polyethylene tubing. Monofilament nylon fibres (diameter: 0.2 mm), 10-cm long each and in a bundle of at least 12 strands, are inserted through the protruding loop of the thread at the end of the polyethylene tubing until their mid-point. The longer ends of the nylon thread on the other side of the tubing are pulled slowly to draw in the fibre bundle. When a distance of 3 cm from the distal end is reached, the remaining exposed fibres are cutoff evenly, and the lead nylon thread is pulled again from the other end of the tubing, until the fibre bundle reaches the middle of the tubing. The nylon lead thread is retrieved by pulling a single piece. The resultant flow moderator then contains, in this case, 24 aligned and even strands of nylon fibre bundle. This flow moderator can provide a flow rate of about 60 mL of water per hour at a driving pressure of 48 kPa. When two such moderators are connected in series, the flow rate will be about 22 mL/hr. A flow rate of about 11 mL/hr can be obtained with 4 connected serially at 48 kPa driving pressure. This is the pressure generated by an equal volume admixture of Freon 11 and Freon 114 which can be used as a propellant for the device of the present invention. Therefore, by removing or by-passing the serially connected moderators, flow rates may be increased from 11 mL/hr to 60 mL/hr in one step. Likewise, by reconnecting or closing the bypass, it is possible to reduce the flow rate from 60 mL/hr to 22 mL/hr or 11 mL/hr. Other monofilament or multifilament synthetic fibres made from polyesters, polyurethane, polyacrylonitrile, poly-(methyl methacrylate) or natural fibres, such as silk, wool, cotton etc., may also be used. However, the synthetic monofilament fibres are preferred, because of their chemical stability, mechanical strength and low swelling tendency in aqueous solution. A high swelling tendency may alter the resistance to flow. In addition to a higher tendency to swelling, the multifilament fibres may release lints or trap microscopic materials in their interstices which would also affect the flow rate. In this regard the inclusion of a 0.22-micron porosity filter unit (diameter: 2.5 cm) between the exit port of the drug solution bag and the flow moderators may help to eliminate any invisible suspension in the solution which can clog the fine channels between the aligned fibre bundle of the flow moderator.

The invention is further described in the following examples, which are presented by way of illustration, and not intended to limit the scope of the invention.

EXAMPLE 1

The middle portion of a 45-cm length of nylon thread (0.3 mm diameter) was coated lightly with beeswax for 15 cm. The thread was then folded at its midpoint and pushed through a 7-cm section of the stem of a flexible polyethylene tubing cut from a disposable pipet (DPTP style D, Bio-Rad Laboratories, Mississauga, Ontario) which has an internal diameter of about 1 mm (wall thickness: 0.7 mm). Monofilament nylon fibres (4-lb weight fishing line; diameter: 0.2 mm), 10 cm in length and in a bundle of 12 strands, are inserted through the protruding thread loop at the end of the polyethylene tubing until their mid-point. The longer ends of the thread on the other side of the tubing are pulled slowly to draw in the fibre bundle. When a distance of 3 cm from the distal end is reached, the remaining strands are cut off evenly at the end of the tubing, and the nylon thread loop is pulled again at the other end until the nylon fibre bundle has reached the middle of the tubing. The lead thread is then retrieved by pulling a single piece slowly. The resultant bundle of fibre then contains, in the present case, 24 aligned and even strands.

To determine the flow rate, the moderator just made is connected to a 16-gauge hypodermic needle attached to a 50-ml capacity syringe which is filled with normal saline. The open top end of the syringe barrel is closed by a size-6 rubber stopper which has a T-joint tube pierced through it. One arm of the horizontal end openings of the T-joint tube is connected to a compressed air cylinder with secondary valves for fine adjustment to obtain low pressure, and the other arm is linked to a low pressure gauge. After checking for leaks, the pressure valve is opened to obtain a reading of 48 kPa on the low pressure gauge. Other pressure readings may be selected to simulate the pressure of a desired propellant to be used later. The liquid drops which appear at the end of the aligned nylon fibre flow moderator are collected in a 100-mL graduated cylinder and the time intervals are noted. Similar flow measurements are also taken with two, three and four moderators, fabricated as just described, connected in series. Typical results are shown in Table 1 below:

TABLE 1

| No. of Moderators Connected in Series | Flow Rate of Aligned Fibre Moderators | | |
|---|---|---|---|
| | Time (min) | Saline Volume Collected (mL) | Flow Rate (mL/hr) |
| 1 | 15 | 14.70 | 58.80 |
| | 30 | 30.40 | 60.80 |
| | 45 | 44.70 | 59.60 |
| | | Average: | 59.73 |
| 2 | 15 | 5.80 | 23.2 |
| | 30 | 11.20 | 22.4 |
| | 45 | 16.20 | 21.6 |
| | | Average: | 22.40 |
| 3 | 15 | 3.20 | 12.80 |
| | 30 | 6.70 | 13.40 |
| | 45 | 10.30 | 13.70 |
| | | Average: | 13.30 |
| 4 | 15 | 2.70 | 10.80 |
| | 30 | 4.80 | 9.60 |
| | 45 | 7.60 | 10.10 |
| | | Average: | 10.20 |

EXAMPLE 2

Two pieces each of the 18 cm×10.6 cm, 18 cm×5 cm, and 10 cm×5 cm panels are cut from a 3-mm thick sheet of poly-(methyl methacrylate). A hole, 3.5 cm long horizontally and 1 cm wide vertically is then cut in the centre of one of the 10 cm×5 cm panels. The two long side panels and the two small end panels are glued perpendicularly onto the 18 cm×10.6 cm bottom panel by the methyl-cyanoacrylate adhesive to form a rectangular box. A polyethylene sac, 18 cm×10 cm×5 cm is formed by heat sealing heavy-duty films along the edges and connected to a identical sac by a length of flexible polyethylene tubing at the end corners. Another length of polyethylene tubing, which is to be used later as the propellant inlet, is attached to the other side of one of the sacs before it is affixed to the bottom of the transparent plastic box, just fabricated, using double-faced adhesive tape. The propellant inlet tubing is pulled through the 3.5 cm×1 cm hole on the 10 cm×5 cm side panel. A 250-mL capacity poly-(vinyl chloride) drug solution infusion container (e.g. Viaflex ® marketed by Travenol Inc., Deerfield, Il.) is filled with 250 mL of a 4% dextrose solution in normal saline through one of the two septum-sealed spouts by a large syringe. Without pulling out the syringe needle, the solution container is gently tapped while held vertically, and the rising bubbles which coalesce to form a pocket of air around the needle tip is aspirated before the needle stem is withdrawn. The filled solution container is placed horizontally on top of the leak-proof polyethylene sac already in the bottom of the rigid plastic box, and the 2 spouts of the solution container are positioned centrally through the 3.5 cm×1 cm side opening. The other leak-proof polyethylene sac is superimposed on top of the poly-(vinyl chloride) solution container and the box is closed by fastening the 18 cm×10.6 cm top cover panel with strips of nylon cord-reinforced adhesive tape around the mid-section and near both ends. One of the septum sealed spouts on the solution container is connected to a section of 4-cm long tubing Tygon ® (I.D.: 3 mm, and O.D.: 6 mm) through a hypodermic needle (20 gauge size) and the other end of the tubing is joined to a 0.22-micron porosity Millipore ® disposable filter (diameter 2.5 cm) through one of the two joints on the filter housing. The other joint is connected to a series of three aligned nylon fibre flow moderators constructed as already described, with 24-strands of 3 cm long monofilament fibre in each. The propellant inlet tubing is then connected to the valve of a 50-mL capacity aerosol canister which is filled with 30 mL of a 1-to-1 admixture of Freon ® 11 and Freon ® 114 by volume. This combination of the volatile fluorocarbon liquid develops a relatively constant pressure of about 48 kPa at ambient temperature and when the canister valve is opened, the fluorocarbon pressure inflates the two leak-proof polyethylene sacs inside the rigid plastic casing. The relatively constant compression exerted on the flexible solution container sandwiched in-between squeezes the dextrose solution in saline through the exit spout, passing through the Millipore ® filter into the three flow moderators connected in series. Drops of solution discharged from the last flow moderator are directed towards the first tube of a tray of 15-ml capacity test tubes arranged in a circular spiral. The automatic fraction collector is programmed to switch to the next tube every 60 min, and the volume of dextrose solution collected will represent the flow rate of the device of the present invention in mL/hr. The result in Table 2 shows that the flow rate is essentially constant up to 200 mL of the 250 mL solution in the flexible Viaflex ® container, i.e., a voiding efficiency of 80% at the constant flow rate expected without the need for any intermittant adjustment. The total volume delivered until flow ceases is 88% of the 250 mL put in the flexible solution container.

TABLE 2

| Delivery Rate from a 250-mL Capacity Solution Container by the Compression Device of the Instant Invention | | |
|---|---|---|
| Time (hr) | Flow Rate (mL/hr) | Total Volume Delivered (mL) |
| 1 | 11.30 | 11.30 |
| 2 | 11.50 | 22.80 |
| 3 | 11.00 | 33.80 |
| 4 | 11.20 | 45.00 |
| 5 | 10.90 | 56.90 |
| 6 | 11.20 | 68.10 |

TABLE 2-continued

Delivery Rate from a 250-mL Capacity Solution Container by the Compression Device of the Instant Invention

| Time (hr) | Flow Rate (mL/hr) | Total Volume Delivered (mL) |
|---|---|---|
| 7 | 11.00 | 79.10 |
| 8 | 11.00 | 90.10 |
| 9 | 11.20 | 101.30 |
| 10 | 11.00 | 112.30 |
| 11 | 10.80 | 123.10 |
| 12 | 11.10 | 134.20 |
| 13 | 11.50 | 145.70 |
| 14 | 11.10 | 156.80 |
| 15 | 10.80 | 167.60 |
| 16 | 11.00 | 178.60 |
| 17 | 10.90 | 189.50 |
| 18 | 10.80 | 200.30 |
| 19 | 8.90 | 209.20 |
| 20 | 6.30 | 215.50 |
| 21 | 4.10 | 219.60 |
| 22 | 1.2 | 220.80 |
| 23 | 0.3 | 221.10 |
| 24 | 0.0 | 221.10 |
| 25 | 0.0 | 221.10 |

EXAMPLE 3

Two pieces each of the 18 cm×10 cm, 18 cm×5 cm, and 10 cm×5.6 cm panels are cut from a 3-mm thick sheet of Acrylite ®(Chemacrylite Limited, Canada). A hole, 3 cm in length longitudinally and 1 cm wide laterally, is cut in the centre of one of the 10 cm×5.6 cm panels. The remaining 5 panels are glued together along the edges by methyl α-cyanoacrylate adhesive to form an 18 cm×10 cm×5 cm vertical rectangular box. The two leak-proof polyethylene sacs are made and connected as described in EXAMPLE 2. After 2 cm×1 cm strips of double-faced adhesive tape are pressed onto the centre of the opposite interior surface of the 18 cm×10 cm panels, the two leak-proof sacs are aligned against the surface of these two panels, and then pressed over the tacky adhesive tape which prevents shifting of the sacs. A 250-mL capacity flexible solution container (Flexpak ® made by DRG Limited, United Kingdom) is filled by syringe with 150 mL of a solution containing 500 mg of tetracycline in phosphate buffered saline at pH 7.4. After the trapped air is aspirated before the syringe needle is pulled out, the Flexpak ® solution container is lowered into the upright rectangular box and positioned evenly between the two leak-proof sacs. The two spouts of the Flexpak ® container and the inlet tubing of the leak-proof sac are held together and threaded through the 3.5 cm×1 cm opening. The top panel is then aligned with the edges of the box and held in position by nylon-cord reinforced adhesive tape on both sides of the 3.5 cm×1 cm opening. One of the septum-sealed spouts on the solution container is connected to a section of 4-cm long silicone tubing (I.D.: 3 mm, O.D.: 6 mm) through a hypodermic needle (22-gauge size), and the other end of the silicone tubing is joined to a 0.45-micron porosity Acrodisc ®CR disposable filter (diameter: 2.5 cm; made by American Scientific Products, McGaw Park, Il.) using one of the two joints on the housing. The other joint is linked to a series of two aligned nylon fibre flow moderators fabricated as aforementioned, with 24-strands of 3-cm long monofilament fibre in each moderator. The propellant inlet tubing of the leak-proof sac is connected to the valve of a 45-ml capacity vinyl-coated glass aerosol bottle filled with an equal volume admixture of Freon ® 13 and Freon ® 114 which has a pressure of 50 kPa at 21° C. The exit end of the second flow moderator unit is connected to a section of 20-cm long Tygon ® tubing, and when drops of the tetracycline solution begin to appear at the end of the tubing, soon after the aerosol canister valve is opened, the automatic fraction collector is started. Since the two flow moderators connected in series will give a flow rae of about 22 mL/hr, the automatic fraction collector is programmed to shift 1 tube space every 30 minutes, thus the flow rate , as shown in Table 3 below, multiplied by 2 will give the flow rate per hour.

TABLE 3

| Performance of the Compression Device of the Instant Invention with a 250-mL Solution Container Filled with 150-mL of a Tetracycline Solution | | |
|---|---|---|
| Time(hr) | Flow Rate/0.5 hr | Total Volume Delivered (mL) |
| 0.5 | 11.70 | 11.70 |
| 1.0 | 11.20 | 22.90 |
| 1.5 | 11.20 | 34.10 |
| 2.0 | 11.20 | 45.30 |
| 2.5 | 10.90 | 56.20 |
| 3.0 | 11.40 | 67.60 |
| 3.5 | 11.60 | 79.20 |
| 4.0 | 11.20 | 90.40 |
| 4.5 | 11.20 | 101.60 |
| 5.0 | 11.30 | 112.90 |
| 5.5 | 11.00 | 123.90 |
| 6.0 | 8.60 | 132.50 |
| 6.5 | 5.10 | 137.60 |
| 7.0 | 1.90 | 139.50 |
| 7.5 | 0.30 | 139.80 |
| 8.0 | 0.00 | 139.80 |
| 8.5 | 0.00 | 139.80 |

The voiding efficiency at constant flow rate is 83% of the total and when flow ceases, measurement shows that 93% of the intitial 150 mL is discharged.

EXAMPLE 4

A 100-mL capacity Flexpak ® drug solution container is filled by a syringe with 100 mL of a 1% sodium nitroprusside solution in saline. The container is then lowered into the upright rectangular box of EXAMPLE 3, the top panel is held in position by adhesive tape, and the two flow moderators preceded by a filter are connected as described in EXAMPLE 3. In addition, a flexible by-pass 48 tube with a pinch clamp 50 is installed between the two flow moderators and connected to the exit end of the second flow moderator with another T-joint. When the pinch clamp is in place, the drug solution will pass through both flow moderators. If a faster flow rate is desired, the pinch clamp is removed and the drug solution will flow through the first flow moderator into the by-pass tube. This flow path avoids the resistance of the second flow moderator, and results in a higher flow rate. Table 4 shows the increase in the flow rate from about 11 mL/0.5 hr to about 15 mL/0.25 hr as determined by the volume of solution in the test tubes placed in the automatic fraction collector aforementioned in EXAMPLES 2 and 3.

TABLE 4

| Increase in Flow Rate Using a By-pass Between Two Flow Moderators | | | |
|---|---|---|---|
| Time | Flow Rate | | Total Volume |
| (hr) | Per 0.5 hr | Per 0.25 hr | Delivered (mL) |
| Two flow moderators operating (i.e., by-pass clamped) | | | |

TABLE 4-continued

Increase in Flow Rate Using a By-pass Between Two Flow Moderators

| Time | Flow Rate | | Total Volume |
|---|---|---|---|
| (hr) | Per 0.5 hr | Per 0.25 hr | Delivered (mL) |
| 0.0 | | | |
| 0.5 | 11.30 | | 11.30 |
| 1.0 | 11.70 | | 23.00 |
| By-pass Unclamped (i.e., only 1st flow moderator operating) | | | |
| 1.25 | | 14.40 | 37.40 |
| 1.5 | | 15.10 | 52.50 |
| 1.75 | | 14.70 | 67.20 |
| 2.00 | | 14.90 | 82.10 |
| 2.25 | | 6.60 | 88.70 |
| 2.50 | | 1.60 | 90.30 |
| 2.75 | | .80 | 91.10 |
| 3.00 | | 0.00 | 91.10 |
| 3.25 | | 0.00 | 91.10 |

In this case, the flow rate remains at the constant level, selected by clamping or unclamping the by-pass tube, until over 82 mL of the 100 mL content is delivered. When the flow ceases, over 91% of the total solution volume is discharged.

It will be understood that the above examples are illustrative only and the invention is not limited thereto.

I claim:

1. A portable external compression device capable of pressing a solution through a flow moderator system for infusion at constant flow rate from a flexible solution container positioned therein comprising a pair of inflatable compartments enclosed in stiff casing disposed as to capture said flexible container therebetween, means to inflate said compartments so as to impose a constant pressure on said flexible container, and a flow moderator system adapted to be connected to an outlet of said flexible container.

2. The compression device of claim 1 wherein the stiff casing comprises an optically transparent plastic material.

3. The compression device of claim 2 wherein the inflatable compartments comprise flexible leak-proof sacs of synthetic polymer film materials.

4. The compression device of claim 3 wherein the stiff casing comprises a plastic material selected from the group consisting of poly-(alkyl acrylate), polyester, polycarbonate, polystyrene, epoxy, poly-(vinyl chloride), polyamide, polyethylene, polypropylene, polyurethane, copolymers or a combination thereof.

5. The compression device of claim 3 wherein the flexible leak-proof sacs comprise polyethylene, poly-(vinyl chloride), polypropylene, polyester, polyurethane, and polyacrylonitrile film materials.

6. The compression device of claim 5 wherein the flow moderator system comprises a tube containing a bundle of aligned fibres.

7. The compression device of claim 6 wherein the flow moderator system comprises a plurality of said tubes connected in series and means to by-pass at least one of said tubes.

8. The compression device of claim 7 wherein the fibres are selected from the group consisting of polyamide, polyester, polypropylene, poly-ethylene, poly(alkyl acrylate), poly-(vinyl chloride), polystyrene, polyurethane, silk, wool, cotton materials or combination thereof.

9. The compression device of claim 8 wherein the tube is selected from the group consisting of polyethylene, polyamide, poly-(alkyl acrylate), poly-(vinyl chloride), polypropylene, polystyrene, polyurethane, poly-(vinyl acetate), silicone or combination thereof.

10. The compression device of claim 9 wherein the flexible leak-proof sacs are inflatable by gas under pressure.

11. The compression device of claim 10 wherein the gas under pressure is generated by admixture of carbonate/dilute acid, methylene chloride/tetramethylsilane, hexane/butane, 1,1,2-trichlorotrifluoroethane/1,2-dichlorotetrafluorethane, trichlorofluoromethane/1,2-dichlorotetrafluorethane or appropriate combination thereof.

12. The compression device of claim 1, wherein said casing is adapted to maintain said inflatable compartments in compression when said compartments are inflated.

* * * * *